United States Patent [19]

Park et al.

[11] Patent Number: 4,918,103

[45] Date of Patent: Apr. 17, 1990

[54] LIQUID ORAL PHARMACEUTICAL COMPOSITIONS OF NON-STEROIDAL ANTI-INFLAMMATORY DRUGS

[75] Inventors: Moo K. Park, Fayetteville, N.Y.; Henry C. Caldwell, Wilmington, N.C.

[73] Assignee: Formulations Development Labs, Wilmington, N.C.

[21] Appl. No.: 223,420

[22] Filed: Jul. 25, 1988

[51] Int. Cl.$^4$ .................. A61K 31/19; A61K 31/255; A61K 31/275; A61K 47/00

[52] U.S. Cl. .................................. 514/520; 514/548; 514/557; 514/569; 514/784; 514/785

[58] Field of Search ............... 514/557, 548, 165, 784, 514/785, 520

[56] References Cited

U.S. PATENT DOCUMENTS

| | | | |
|---|---|---|---|
| 4,079,131 | 3/1978 | Lin et al. | 514/770 |
| 4,571,400 | 2/1986 | Arnold | 514/557 |
| 4,681,897 | 7/1987 | Brand | 514/557 |
| 4,684,666 | 8/1987 | Haas | 514/557 |
| 4,719,239 | 1/1988 | Muller et al. | 514/785 |
| 4,722,941 | 2/1988 | Eckert et al. | 514/784 |

OTHER PUBLICATIONS

*The Merck Manual*, 15th Ed. (1987), pp. 1242-1245 and 2506-2515.

*Facts and Comparisons*, (12-1976), pp. 605-606.

*Primary Examiner*—Stanley J. Friedman
*Attorney, Agent, or Firm*—William H. Edgerton

[57] ABSTRACT

A pharmaceutically elegant, one phase, liquid composition for oral administration comprises a NSAID such as ibuprofen plus a di- or triglyceride of a medium chain fatty acid edible oil which has the characteristics of a pharmaceutical solvent carrier as known to those skilled in the art. Other pharmaceutical additives may be optionally added. An additional stipulation is that ethanol or other monohydric alcohol solvents should not be present.

14 Claims, No Drawings

LIQUID ORAL PHARMACEUTICAL COMPOSITIONS OF NON-STEROIDAL ANTI-INFLAMMATORY DRUGS

BACKGROUND OF THE INVENTION

Liquid oral pharmaceutical compositions for oral administration have been often formulated in the past in vehicles which contain ethanol. Frequently, the compositions thusly prepared do not contain water because of a stability problem, to suppress undesirable organoleptic properties of the composition or to enhance solubility.

Ibuprofen is a nonsteroidal anti-inflammatory (analgesic) drug whose family is known in the art as NSAID's. It has been on the ethical and proprietary markets for years and is in widespread use. While many dosage unit forms of the compound are on the market, few acceptable oral, one phase liquid forms of ibuprofen have been reported. U.S. Pat. No. 4,684,666, U.S. Pat. No. 3,228,831 and U.K. Patent Specification 971,700, are representative of the prior art.

Due to the low solubility of ibuprofen in aqueous vehicles and its poor organoleptic characteristics, certain of us earlier found excellent oral dosage units can be prepared using a vehicle comprising certain edible oils and absolute ethanol. However, now a new problem has been identified.

Ibuprofen, and other NSAID's which have a reactive carboxylic acid moiety in their chemical structures, have been unexpectedly found to form ethyl ester derivatives in the oral edible oil-alcohol vehicles.

Esterification can reduce the quantity of ibuprofen available for absorption. The alcohol-oil vehicles remain, however, excellent products organoleptically when formulated with NSAID active ingredients. The following description will describe a solution we have found to this previously unrecognized problem in the art.

SUMMARY OF THE INVENTION

This invention comprises a one-phase, liquid pharmaceutical composition for oral administration which comprises a NSAID medicament whose molecular structure contains a reactive carboxylic acid group, a synthetic edible oil glyceride of one or more mid-range fatty acids and optional pharmaceutical additives with the provision that ethanol is not substantially present. Said invention solves the problem described above which is related to the chemical stability of ibuprofen in certain oily vehicles containing ethanol. This invention also fills the need for an oral solution of ibuprofen or other NSAID's which has an acceptable oral organoleptic property for patients. Specifically, this invention provides a single phase, non-aqueous, non-alcoholic liquid composition of ibuprofen for oral administration.

The essential ingredients of the pharmaceutical composition of this invention are:

(A) About 1% to about 10% w/v of a NSAID such as ibuprofen; and
(B) About 60% to 99% v/v of an edible oil of the group of mid range fatty acid glycerides; plus the absence of any substantial quantity of ethanol.

This invention depends on the discovery of a small group of liquid, edible liquids which are synthetic or semi-synthetic in nature and in which the NSAIDs such as ibuprofen are sufficiently soluble to give adequate and convenient dosage units for liquid oral dosage, yet do not require the presence of alcohol to give good taste and stability.

This invention also provides a method of treating a human with ibuprofen by orally administering to the human, a non-aqueous, alcohol free pharmaceutical composition of this invention. The pharmaceutical composition of the invention is in the form of solutions which can be maintained in a single phase over a range of temperatures. The composition has a pleasant taste and can be formulated to avoid irritation of oral mucosa.

DETAILED DESCRIPTION OF THE INVENTION

The one phase, liquid pharmaceutical compositions for oral adminstration of this invention comprise a solution of a NSAID, such as ibuprofen and an edible oil of the mid range fatty acid glyceride group in the absence of ethanol. Optional adjuvants, such as flavors, local anesthetics, sweeteners, antimicrobial agents, colorants, antioxidants, or surfactants can be incorporated in the oral compositions of the invention.

It has been found that aqueous vehicles for NSAID's especially ibuprofen, pose unacceptable taste problems or crystal growth during the storage period. These problems are often present with pharmaceutical compositions in aqueous solution or suspension form.

We previously discovered that certain non-aqueous vehicles comprising certain edible oils and absolute ethanol plus other optional additives provide acceptable solutions for most of the problems associated with oral aqueous compositions of NSAID medicaments. Taste of the non-aqueous composition becomes acceptable and irritation of the oral mucosa disappears.

We have now found that when these prior compositions contain ethanol as it was thought necessary, there can be an esterification reaction occurring between ibuprofen and ethanol. The degree of ester formation increases with amount of alcohol and storage temperature. (See Table II). Esterification can reduce the availability of the active medicament to the body or affect the elegance of the pharmaceutical form.

TABLE I.

Ibuprofen Formulas Used for Chemical Stability Evaluation

| Formula #/ Ingredient | #229 | #265 | #241-B | #209 | #282 |
|---|---|---|---|---|---|
| Ibuprofen | 4 | 4 | 4 | 4 | 4 |
| Saccharin | 0.02 | 0.02 | 0.05 | 0.3 | 0.3 |
| Menthol | 0.24 | 0.24 | 0.24 | 0.24 | 0.24 |
| Eucalyptus Oil | 0.08 | 0.08 | 0.08 | 0.08 | 0.08 |
| Cinnamon | 1 | — | — | — | — |
| Fruit Mint | 0.7 | — | — | — | — |
| Spice Mint | — | — | 0.2 | — | — |
| Polysorbate 85 | — | 2 | — | — | — |
| Ethanol 100% | — | — | 1 | 10 | 10 |
| "Miglyol 810"* q.s. ad | 100 | 100 | 100 | 100 | 100 |

*Brand name of caprylic/capric triglyceride sold by Dynamit Nobel, West Germany.

TABLE II

Chemical Stability of Ibuprofen

| Formula #/ Storage Condition | #229 | #265 | #241-B | #209 | #282 |
|---|---|---|---|---|---|
| Initial | 100% | 100% | 100% | 100% | 100% |
| ½ month @ 75 C | 100% | 100% | — | 80.5% | — |
| 1 month @ 45 C | 99.6% | — | — | 93.7% | 92.5% |

TABLE II-continued

| Formula #/ Storage Condition | #229 | #265 | #241-B | #209 | #282 |
|---|---|---|---|---|---|
| Chemical Stability of Ibuprofen | | | | | |
| 4 months @ 45 C | 98% | — | 92.3% | — | — |

When ibuprofen is dissolved in an edible oil as described hereafter, such as caprylic/capric triglyceride, no evidence of ester formation was detected as shown in Table II. Only when ethanol is present is there a chemical instability. Similar problems of ester formation potentially exist for other medicaments whose structures contain a chemically reactive carboxylic group. These drugs are also formulated in the described non-aqueous vehicle containing no ethanol to prevent the ester formation.

Nonsteroidal anti-inflammatory drugs (NSAID's) which have carboxylic functional groups and are formulated in these non-aqueous vehicles containing no ethanol are as follows:

(1) Salicylic Acid Derivatives Aspirin, Diflunisal.
(2) Anthranilic Acid Derivatives Mefenamic Acid, Flufenamic Acid.
(3) Indoleacetic Acid Derivatives Indomethacin.
(4) Indeneacetic Acid Derivatives Sulindac.
(5) Pyrroleacetic Acid Derivatives Tolmetin.
(6) Phenylacetic Acid Derivatives Ibuprofen, Fenoprofen.
(7) Naphthaleneacetic Acid Derivatives Naproxen.

The pharmaceutical composition of this invention primarily contains the medicament in a pharmaceutically effective amount. The concentration of the medicament in the composition will vary with the medicament, the desired therapeutic effect and the size of the dosage administered to the patient. For example, the pharmaceutical composition will contain the medicament in an amount within dosage unit ranges approved by the Food and Drug Administration for over-the-counter sale or within dosage unit ranges listed the Physician's Desk Reference.

A practical dose range for ibuprofen oral liquid is from about 50 mg to about 500 mg/5 ml, which corresponds to about 1% to about 10% w/v ibuprofen in the composition. This is a teaspoon amount and is administered orally as needed from 1-6 times daily.

The pharmaceutical composition of the invention can be packaged in unit dosage form or in larger quantities with instructions for obtaining a unit dosage. Usually, as noted above, a dosage unit is contained in a teaspoon quantity of the pharmaceutical composition which is administered orally as often as needed within the approved daily dose range for the medicament to a patient in need of anti-inflammatory analgesic treatment.

The synthetic or semi-synthetic edible oils which are becoming available to the market as equivalents of vegetable oils are employed in this invention as the second essential ingredient. These edible oils include the "Olestras" (or sugar fatty acid esters) and the preferred "Miglyols" (or fatty acid esters of open chain polyols). Synthetic edible oils are very useful because of their purity and favorable physical characteristics. Examples of such synthetic oils are the esters and mixed esters of glycerol or propylene glycol (called herein "glycerides"), especially the tri- or diglycerides of medium chain fatty carboxylic acids. More specifically, the $C_6$-$C_{12}$ fatty acid glycerides, and especially the $C_8$-$C_{10}$ fatty acid triglycerides are used. Said esters must, of course, have satisfactory pharmaceutical and physical properties.

The triglycerides of the $C_8$-$C_{10}$ fatty acids of fractionated coconut oil are particularly preferred. A species of this subgroup of edible oils is commercially available under the trade name "Miglyol", which is a triglyceride of caprylic acid and capric acid with glycerol. This composition meets the requirements of the British Pharmacopoeia 1980, Addend. 1983, for the monograph "Fractionated Coconut Oil" and of the German Pharmacopoeia, DAB 8, for the monograph "Medium Chain Triglycerides". These synthetic oils have been used to prepare other pharmaceutical products previously but not, to the best of our knowledge, to prepare one phase oral composition. Palmitic, linoleic, succinic or oleic acid glycerides may also be used if they have the proper solvent properties. The oil is the major ingredient of the described medium and is selected from the range of 60-99% v/v, preferably 90-97% v/v.

The second essential component of the oral dosage units of this invention described above, the edible oil, is used as the major ingredient of the composition. It is used to "make-up" the solution to the proper volume after the therapeutic agent (the NSAID) is mixed with the optional additives described hereafter.

TABLE III

| Organoleptic Evaluation of Ibuprofen Formulations | | |
|---|---|---|
| Formulation | Taste | Irritation |
| 4 w/v % Ibuprofen aqueous solution in Na Salt form | Unacceptable | Burning sensation on oral mucosa |
| 4 w/v % Ibuprofen aqueous suspension | Unacceptable | Burning sensation on oral mucosa |
| 4 w/v % Ibuprofen in Dehydrated Ethanol/ "Miglyol 810" (10/90 v/v %) | Taste improved | Burning sensation reduced |
| 4 w/v % Ibuprofen in "Miglyol 810" | Taste improved | Burning sensation reduced |

Irritation of oral mucosa can be entirely eliminated by the use of effective amounts of topical oral anesthetics.

It will be understood that nontoxic flavoring agents can be included in the pharmaceutical compositions to impart a sweet, sour, salty or spicy taste. Examples of flavors are fruit, mint, vanilla, chocolate, cinnamon, licorice, and root flavors. A combination of flavoring agents is generally effective in masking most unpleasant taste sensations.

The liquid pharmaceutical composition of this invention can also contain other adjuvants, such as antimicrobial agents (although these are not usually needed as the vehicle is non-aqueous), colors, antioxidants or surfactants. Color selection can be made consistent with flavor. Surfactant selection can be made from a group of nonionic-nontoxic surfactants such as macrogol esters, polysorbates 20, 40, 60, 80 and 85, and mono- and diglycerides of $C_{12}$-$C_{18}$ fatty acids to expedite the dispersion of a pharmaceutical composition in the gastrointestinal tract. The lowest level of surfactant necessary is usually used. The surfactant may also be used to increase the solubility of the NSAID component in the medium. If the taste of the surfactant is objectionable, the addition of a sweetening agent such as sucrose or sorbitol has been found to be especially useful.

It will be understood that the pharmaceutical composition can be made translucent or even opaque by the addition of adjuvants, provided that the amount of the adjuvants does not adversely affect the miscibility of the vehicle and medicament, the stability of the pharmaceutical composition, or its organoleptic properties.

The selection of such pharmaceutically acceptable materials and their use in the pharmaceutical composition of the invention is within the level of skill in the art except where described otherwise herein.

The compositions are prepared by mixing the ingredients in any order. The ingredients can be mixed using conventional manufacturing equipment. Most conveniently, the liquid vehicle is prepared in a mixer and the medication added thereto followed by flavoring additives. A purification step can be employed to achieve maximum clarity. The one phase, liquid pharmaceutical composition can then be filled into bottles for sale. The stability of the ingredients is excellent because of the absence of water.

As described above, the present invention is based on discovering a problem with certain useful one-phase, pharmaceutically elegant oral pharmaceutical compositions which contain nonsteroidal, anti-inflammatory analgesic agents. That problem has now been solved by eliminating one essential element of the prior art vehicle and employing one of a sub group of selected edible oils for the vehicle which unexpectedly replace the two ingredient vehicles of the prior art.

The following embodiments of this invention are designed to illustrate the specific use of this invention, but not to limit the scope of invention.

EXAMPLE I

Liquid Ibuprofen Composition

The formulations shown in the table below were prepared as follows. First the vehicles was placed in a mixing vessel equipped with a stirrer, and then the medicament and adjuvants were added and mixed with the vehicle. The edible oil was added to bring the volume to 100 ml. The mixture was constantly stirred until a clear solution was obtained. The clear solution was passed through a 10-micron depth filter and packaged into proper size glass bottles for sale. One teaspoonful can be orally administered to a subject in need of treatment as often as needed and as known and accepted by the medical art to be available for the individual patient.

|                     | #1      | #2      | #3      |
|---------------------|---------|---------|---------|
| Ibuprofen U.S.P.    | 1 g.    | 4 g.    | 8 g.    |
| Saccharin N.F.      | 0.02 g. | 0.02 g. | 0.02 g. |
| Menthol U.S.P.      | 0.2 g.  | 0.2 g.  | 0.2 g.  |
| Eucalyptus Oil N.F. | 0.1 ml  | 0.1 ml  | 0.1 ml  |
| Polysorbate 85      | —       | 2 g.    | —       |
| "Miglyol 810" q.s. to | 100 ml | 100 ml | —       |
| "Miglyol 840" q.s. to* | —    | —       | 100 ml  |

*Brand name of propylene glycol dicaprylate/dicaprate by Dynamit Nobel, West Germany.

Each of these preparations is administered orally by from 1-6 teaspoons per day to a patient in need of anti-inflammatory analgesic activity.

EXAMPLE II

Liquid Ibuprofen Composition

The formulations shown in the table below were prepared as follows. The edible oil, Miglyol 810, was placed in a mixing vessel equipped with a stirrer, and then the medicament was added and mixed to make a clear solution. Adjuvants were then added to the clear ibuprofen solution and the mixture was homogenized. The formulas contain the medicament completely dissolved in the vehicle. The undissolved excipients provide excellent taste and mouth feel. One teaspoonful can be orally administered to a subject in need of treatment as often as needed and as known and accepted by the medical art to be available for the individual patients.

|                       | #4     | #5     | #6     | #7      | #8     |
|-----------------------|--------|--------|--------|---------|--------|
| Ibuprofen U.S.P.      | 4 g    | 4 g    | 4 g    | 4 g     | 4 g    |
| Sodium Saccharin U.S.P. | 0.3 g | —     | —      | 0.3 g   | 0.3 g  |
| Saccharin N.F.        | —      | 0.2 g  | 0.3 g  | —       | —      |
| Tandem 552* 1 g       | 1 g    | —      | —      | 1 g     | —      |
| Arlacel 186**         | —      | —      | —      | 0.75 g  | —      |
| Polysorbate 60 N.F.   | —      | —      | —      | 0.25 g  | —      |
| Polysorbate 85        | —      | —      | 0.5    | —       | —      |
| Sucrose N.F.          | —      | 30     | —      | —       | —      |
| Mannitol U.S.P.       | —      | —      | —      | 30      | —      |
| Sorbitol N.F.         | 20     | —      | —      | —       | —      |
| Spearmint             | —      | —      | 0.3    | —       | 0.5    |
| Artifical Fruit Flavors | 0.4  | —      | —      | —       | —      |
| Peppermint Oil N.F.   | —      | 0.1    | —      | 0.1     | —      |
| Cab-O-sil EH-5***     | 0.5    | 0.5    | 0.5    | 0.5     | 0.5    |
| Miglyol 810 q.s add   | 100 ml | 100 ml | 100 ml | 100 ml  | 100 ml |

*Brand name of a food grade emulsifier blend of mono- and diglycerides and polysorbate 60 (36%) manufactured by Witco Corporation, Memphis, Tennessee.
**Brand name of a emulsifier blend of glycerol monooleate and propylene glycol manufactured by ICI Americas Inc., Wilmington, Delaware.
***Brand name of amorphous fumed silica manufactured by Cabot Corp. Tuscola, Illinois.

Formula #5 using an excess of sucrose is especially useful and acceptable for pharmaceutical elegance.

We claim:

1. A single phase, non-aqueous, liquid dosage unit pharmaceutical composition for oral administration comprising a therapeutic but nontoxic dose of a nonsteroidal anti-inflammatory agent selected from the group consisting of a phenylacetic acid derivative, a indeneacetic acid derivative and a naphthaleneacetic acid derivative and an edible oil comprising an ester of glycerol or propylene glycol with 2 or 3 $C_6$–$C_{12}$ fatty acids in the absence of ethanol.

2. The pharmaceutical composition of claim 1, wherein the nosteroidal anti-inflammatory agent is ibuprofen.

3. The pharmaceutical compositionof claim 2, wherein ibuprofen is in an amount of about 1% to about 10% w/v.

4. The pharmaceutical composition of claim 2, wherein the ester is caprylic, capric triglyceride, propylene glycol dicaprylate or propylene glycol dicaprate.

5. The pharmaceutical composition of claim 3, wherein the amount of edible oil is about 60% to about 99% v/v.

6. The pharmaceutical composition of claim 5, wherein the composition includes a sweetening agent selected from the group consisting of sucrose, sorbitol, saccharin or the calcium salt of saccharin soluble in the edible oil in an amount sufficient to impart a sweet flavor to the composition.

7. The pharmaceutical composition of claim 5, where in the composition contains at least one nontoxic, topical anesthetic selected from the group consisting of menthol or eucalyptus oil in an amount sufficient to produce an anesthetic effect on the sensory receptor organs of taste.

8. The pharmaceutical composition of claim 5, wherein the composition contains a nontoxic, nonionic surfactant selected from the group consisting of a macrogol ester, polysorbate, mono- or diglyceride of a $C_{12}$–$C_{18}$ fatty acid in an amount sufficient to impart a sweet taste to the composition.

9. The pharmaceutical composition of claim 7, comprising:
about 0.06% to about 0.48% w/v menthol; and about 0.02% to about 0.16% v/v eucalyptus oil.

10. The pharmaceutical composition of claim 8, comprising:
about 0.1% w/v to about 4% w/v polysorbate 85;
about 0.1% w/v to about 2% w/v polysorbate 20; or
about 0.1% w/v to about 2% w/v polysorbate 80.

11. The pharmaceutical composition of claim 1, comprising:
about 1% to about 10% w/v ibuprofen;
about 0.02% w/v saccharin;
about 0.2% w/v menthol;
about 0.1% v/v eucalyptus oil; and
about 90% to about 99% v/v caprylic/capric triglyceride.

12. The pharmaceutical composition of claim 1, comprising:
about 1% to about 10% w/v ibuprofen;
about 0.02% w/v saccharin;
about 0.2% w/v menthol;
about 0.1% v/v eucalyptus oil;
about 2% v/v polysorbate 85; and
about 88% to about 97% v/v caprylic/capric triglyceride.

13. The pharmaceutical composition of claim 8 in which from about 10–40 g of sucrose is present in 100 ml of the composition.

14. A method of treating a human in need of anti-inflammatory or analgesic treatment with ibuprofen, wherein the method comprises: orally administering to said human an ibuprofen containing oral composition of claim 2.

* * * * *